United States Patent [19]

Takahashi

[11] Patent Number: 5,356,399
[45] Date of Patent: Oct. 18, 1994

[54] OSTOMY APPLIANCE

[75] Inventor: Tetsuya Takahashi, Kawasaki, Japan

[73] Assignee: Alcare Col, Ltd., Tokyo, Japan

[21] Appl. No.: 837,354

[22] Filed: Feb. 14, 1992

[30] Foreign Application Priority Data

Feb. 15, 1991 [JP] Japan .............. 3-012846[U]

[51] Int. Cl.⁵ .............................. A61F 5/44
[52] U.S. Cl. ................... 604/339; 604/332; 604/338
[58] Field of Search .............. 604/332–345

[56] References Cited

U.S. PATENT DOCUMENTS

| | | | |
|---|---|---|---|
| 2,205,270 | 6/1940 | Perry | 604/337 |
| 3,398,741 | 8/1968 | Hoopes | 604/340 |
| 4,664,661 | 5/1987 | Ferguson | 604/342 |
| 4,710,183 | 12/1987 | Steer | 604/344 |
| 4,872,869 | 10/1989 | Johns | 604/342 |
| 4,973,323 | 11/1990 | Kaczmarek et al. | 604/339 |
| 5,125,917 | 6/1992 | Whealin | 604/331 |

FOREIGN PATENT DOCUMENTS

| | | |
|---|---|---|
| 0468148 | 9/1950 | Canada ................. 604/338 |
| 0098718 | 6/1983 | European Pat. Off. . |
| 0235563 | 6/1983 | European Pat. Off. . |
| 0251502 | 6/1987 | European Pat. Off. . |
| 1266929 | 4/1968 | Fed. Rep. of Germany ...... 604/339 |
| 2845219 | 4/1979 | Fed. Rep. of Germany ...... 604/336 |
| 2179556 | 11/1983 | United Kingdom . |
| 2193097 | 7/1987 | United Kingdom . |
| 2193893 | 8/1987 | United Kingdom . |
| 2198953 | 11/1987 | United Kingdom . |
| 9118566 | 12/1991 | World Int. Prop. O. .......... 604/337 |

OTHER PUBLICATIONS

Stoma Cap, Hollister Product Data Sheet, copyright 1982.

Primary Examiner—Randall L. Green
Assistant Examiner—Bob Clarke
Attorney, Agent, or Firm—Haverstock, Garrett & Roberts

[57] ABSTRACT

Ostomy appliance for attachment around an aperture or opening of the human body including a first member having an adhesive plate fixably positionable by adhesion around the aperture of the human body, a first flange having an annular or ring-form fitting portion around an aperture extending through the adhesive plate, the first flange having a collar or tab extending outwardly from at least a portion of the fitting portion thereof, the collar or tab forming at least one cut-away recess or notch or truncated portion extending to the outermost peripheral edge of the fitting portion, a second member having a second flange with an annular or ring-form fitting portion cooperatively engageable with the first fitting portion, the second member having a bag portion or a cap portion associated with the side thereof opposite the second fitting portion, the cut-away recess or notch being of such a size as to enable the insertion of a finger therein for guiding the first and second members into engagement with each other.

12 Claims, 3 Drawing Sheets

OSTOMY APPLIANCE

Applicant hereby claims foreign priority benefits under 35 U.S.C. §119 of corresponding Japanese patent application Serial No. (Hei) 3-12846 filed Feb. 15, 1991.

1. Industrial Field Of Utilization

The present invention relates to an ostomy appliance which is easily securable to an aperature or opening formed on the surface of a human body, the appliance being usable for such purposes as receiving and collecting waste products expelled from the inside of the human body and also for introducing a liquid preparation into the human body.

2. Background Of The Invention

So-called ostomy appliances are generally furnished for receiving and holding various waste products and waste liquids discharged from the human body and such appliances are sometimes used for introducing a liquid preparation into the human body for therapy or washing at an aperture or opening formed on or through the surface of the human body such as the fistula formed on the surface of the body by performing surgical operations wherein such devices are used to combat rectal or bladder disease. Other applications include use in connection with a leading enteric canal, a ureter tube or other tube connected to the body surface or opening formed on the surface of the human body by a wound. Artificial anal appliances and artificial urinary bladder appliances are typical examples. Since ostomy appliances are to treat waste products discharged from the human body, it is necessary to perform such removal sanitarily without contacting such waste products with the skin or the opening while at the same time maintaining the sanitary reliability of the device such that such waste products do not leak out during use. It is also important that such appliances be easy to put on and to take off and that they are comfortable to the skin since such devices are secured directly to the skin surface.

Various ostomy appliances have heretofore been devised and broadly employed for use in attempting to satisfy the above-described objects and requirements including an ostomy appliance proposed by the present applicant. See U.S. Pat. application Ser. No. 708,477, filed May 31, 1991 corresponding to Japanese Utility Model Application No. (Hei) 2-59606. Such previous ostomy appliances comprise an adhesive plate member having an aperture or opening extending therethrough and adhesive material on one side thereof around the aperture or opening enabling the adhesive plate member to be fixed by adhesion around an aperature or opening of a human body. The adhesive plate member includes a first flange extending around the aperture therethrough on the non-adhesive side of the member. A second member has a second flange capable of detachably fitting to the first flange on the adhesive plate member, which second flange has an aperture or opening extending therethrough which communicates with a pouch or bag attached to the second flange, which pouch or bag receives waste products discharged through the aperture in the human body. The first and second flanges respectively include fitting means such as, for instance, a prominence and a groove which are annular or ring-shape and are cooperatively engageable for attachment of the second or bag member to the first or adhesive plate member.

When the waste products are accumulated in the bag or pouch, the second flange can be disengaged from the first flange to remove the pouch or bag member from the adhesive plate member on the human body. The waste products can then be removed from the bag and the bag either washed for re-use, or alternatively, replaced with a totally new second member. The pouch or bag member can also alternatively be replaced by a cap-type or other type member, as desired.

In such known ostomy appliances, the first flange and the second flange are joined by pressing together the respective fitting means. To avoid pressing against the skin of the wearer when attaching the second member to the first member, it is desirable to construct such ostomy appliances such that a finger can be inserted between the first flange and the adhesive plate so as to be able to sufficiently support and provide backing for the first flange during attachment. To this end, the outer diameter of the first flange is made relatively large.

Such known devices have several shortcomings which limit their desirableness and usefulness as effective, sanitary, comfortable and easy to use appliances. For example, when attempting to position the respective flanges of the known ostomy appliances for engagement or attachment thereof, it is difficult for the user or patient to directly visually confirm the relative positions of the flanges, and thus the patient has to gropingly or by feel position the flanges in many cases. Additionally, as the opening or aperture on the human body is often located on the lower half of the body, positioning of the relative flanges can be made further difficult.

SUMMARY OF THE INVENTION

Means for Solving the Problem

The ostomy appliance according to the present invention comprises a first member having an adhesive plate (skin-contacting plate) fixable by adhesion around the aperture or opening of a human body. A first flange is attached to the adhesive plate member and is located adjacent to the non-adhesive side thereof, and a second member including a second flange capable of fitting or cooperatively engaging the first flange can be detachably fitted to the first member. The adhesive plate has an aperture or opening which corresponds to the aperture or opening of the human body. The first flange is attached or joined to the adhesive plate member directly or through a member having an annular shape such as a washer made of soft plastic and which flange extends outwardly or radially from the aperture in the adhesive plate nearly adjacent to and along the surface of the adhesive plate. On the side of the first flange opposite the adhesive plate, fitting means such as a ring-form or annular fitting portion are provided. Adjacent the outer periphery or peripheral edge of the fitting means is located a collar or tab. The collar or tab includes means for aligning the first and second flanges, which alignment means can comprise one or more cutaway recesses or notches or truncated portions formed in the collar or tab, the recess or notch or truncated portion extending inwardly to adjacent the outermost periphery of the fitting portion and being of such a size as to allow the insertion of a finger thereinto. The second flange also includes corresponding fitting means such as a ring-form or annular fitting portion on one side thereof dimensioned to fit or cooperatively engage the fitting portion of the first flange, and a pouch or bag or cap on the opposite side thereof.

Operation

When the first and second fitting means are to be fitted or coupled together, a finger can be inserted into the notch of the collar and located adjacent the outer periphery of the first flange, whereby the position of the fitting portion of the first flange member is clearly perceived. The second flange can then be located, by feel, in alignment with the first flange and guided into cooperative engagement with the first flange. Furthermore, by inserting one or more fingers between the collar or tab of the first flange and the adhesive plate, the fitting portions of both flanges can be pressed together, the first flange being supported with the fingers. The second flange can be detached from the first flange by grasping the collar of the first flange and the second flange with the fingers and pulling the flanges apart in the conventional manner without allowing the pulling force to act on the adhesive plate.

It is therefore a principal object of the present invention to provide means facilitating the alignment and fitting together of the respective members of an ostomy appliance.

Another object is to provide an ostomy appliance having means enabling the attachment of an ostomy bag to an adhesive plate adhered to a patient by feel alone.

Another object is to provide an ostomy appliance wherein a single finger can be used for aligning and guiding the respective first and second members of the ostomy appliance into engagement with each other.

DETAILED DESCRIPTION OF THE PREFERRED EMBODIMENTS

Practical embodiment of the present device will now be described hereinbelow with reference to the drawings.

Figure 1A:
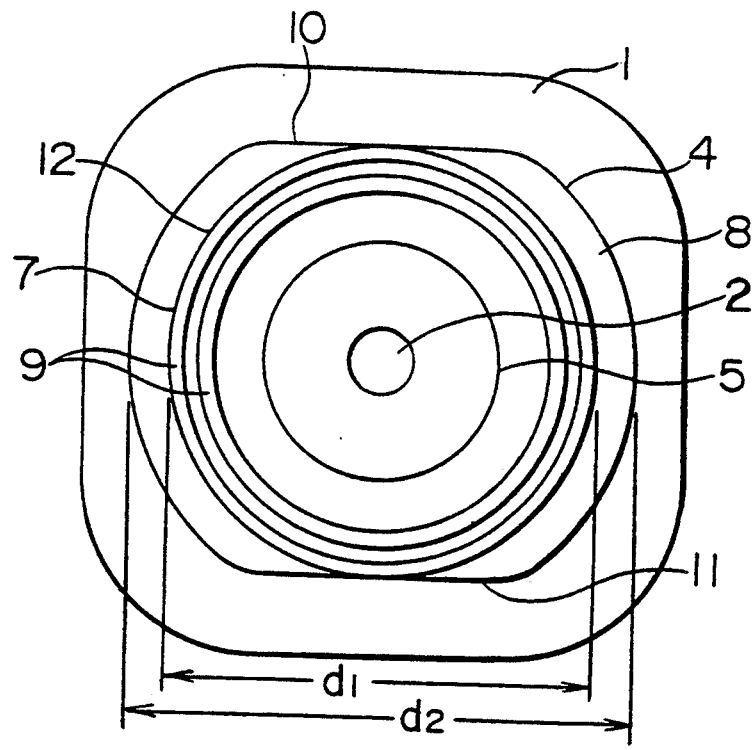
FIGS. 1(a) and 1(b) are each front elevational views showing first and second members, respectively, of an ostomy appliance constructed according to the teachings of the present invention.
Figure 2:
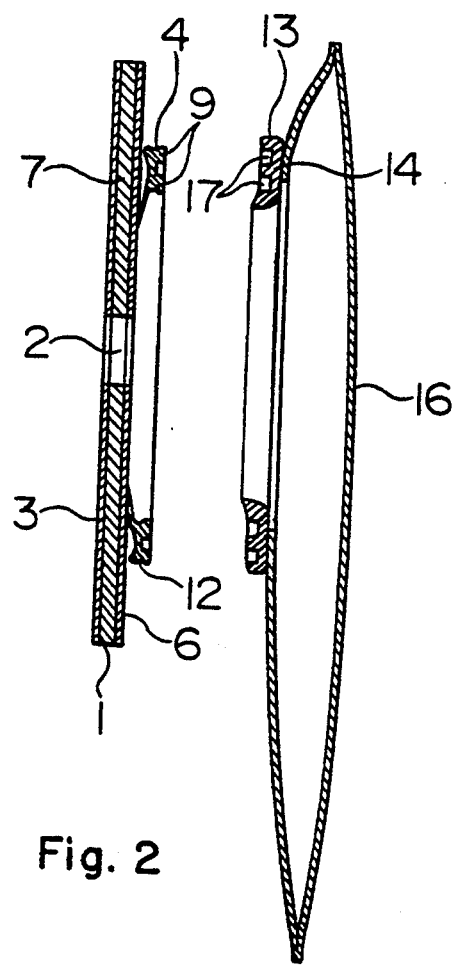
FIG. 2 is a cross-sectional view of the first and second members of the ostomy appliance of FIG. 1 shown in alignment for being joined together.

Referring to the drawings more particularly by reference numbers wherein like numerals refer to like parts, numeral 1 in FIG. 1(a) denotes a first or adhesive plate member comprising an adhesive plate for attaching to the skin of a patient, which member is shown for instance as being square in shape, and has an opening or aperture 2 positioned in approximately the center thereof. Referring briefly to FIG. 2, the adhesive plate member 1 includes an adhesive layer 3 on a side thereof designated as the adhesive side. Numeral 4 denotes a first flange portion of the first member, which first flange portion 4 is preferably concentrically positioned with respect to the opening 2 on the adhesive plate by means of an annular inner periphery 5 which is fixedly or otherwise attached to the adhesive plate, for example, by welding the inner periphery 5 to the surface of the non-adhesive side of the adhesive plate. The first flange 4 extends radially outwardly from the annular inner periphery 5 adjacent to and nearly along the non-adhesive side 6 of the adhesive plate. Fitting means such as an annular or ring-form fitting portion 7 are provided on the side of the first flange 4 opposite the non-adhesive side 6 of the adhesive plate. A collar or tab 8 comprises the radially outermost portion of the first flange 4, which collar or tab 8 is located outwardly of the fitting portion 7. The fitting portion 7 can consist of any suitable fitting means, such as a pair of annular or ring-form projections or prominences 9. The collar or tab 8 can include any desired number of cut-away recesses, notches or truncated portions, such as shown at 10 and 11, formed for instance by linearly cutting away opposing portions of the collar or tab 8 in such a manner that the cut-away recesses or truncated portions 10 and 11 reach or extend inwardly to the outermost periphery 12 of the fitting portion 7. The external diameter $d_1$ of the fitting portion 7, as measured between opposing portions of the outermost peripheral edge 12 of the fitting portion 7 is purposefully smaller than the external diameter $d_2$ of the first flange 4, as measured between opposite outermost peripheral edge portions of the collar or tab 8.

Figure 1B:
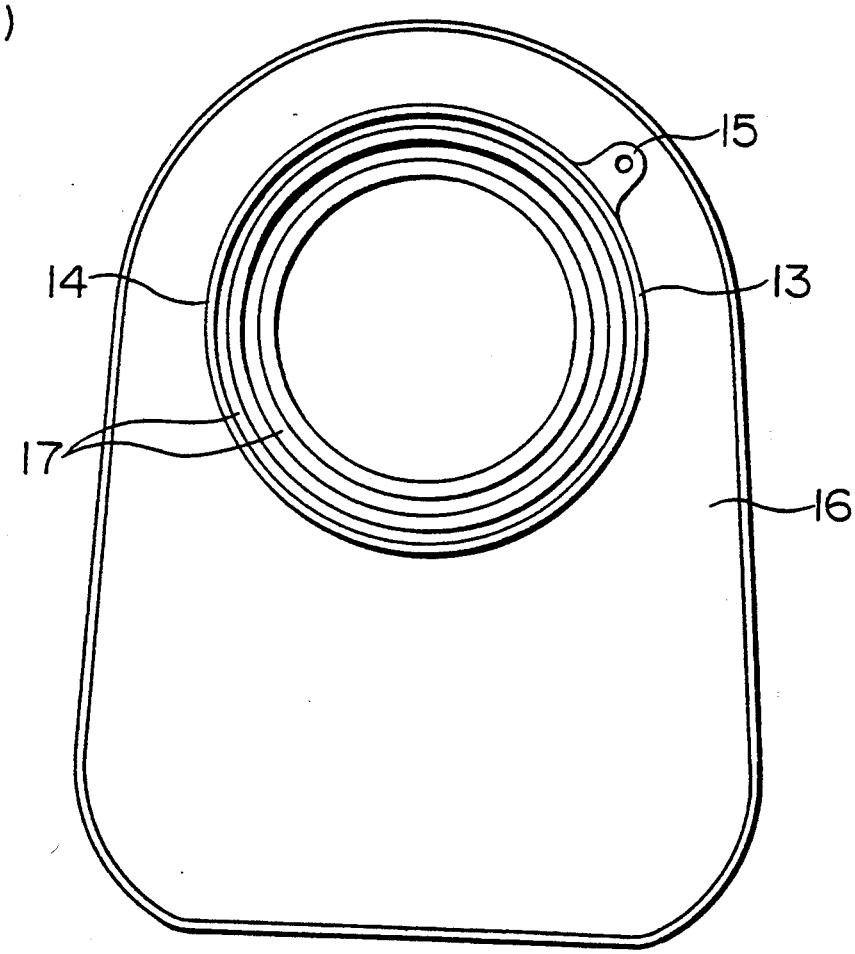

Numeral 13 denotes a second flange, which second flange 13 includes fitting means such as an annular or ring-form fitting portion 14 on one side thereof, as shown in FIG. 1(b) and in FIG. 2. A tab 15 extends radially outwardly from the annular or ring-form fitting portion 14. A pouch or bag 16 is attached to the second flange 13 on the side thereof opposite the annular or ring-form fitting portion 14. The fitting portion 14 is cooperatively engageable with the fitting portion 7 of the first member 1, for instance including a pair of annular grooves 17 into which the projections 9 of the fitting portion 7 are cooperatively insertable.

Figure 3:
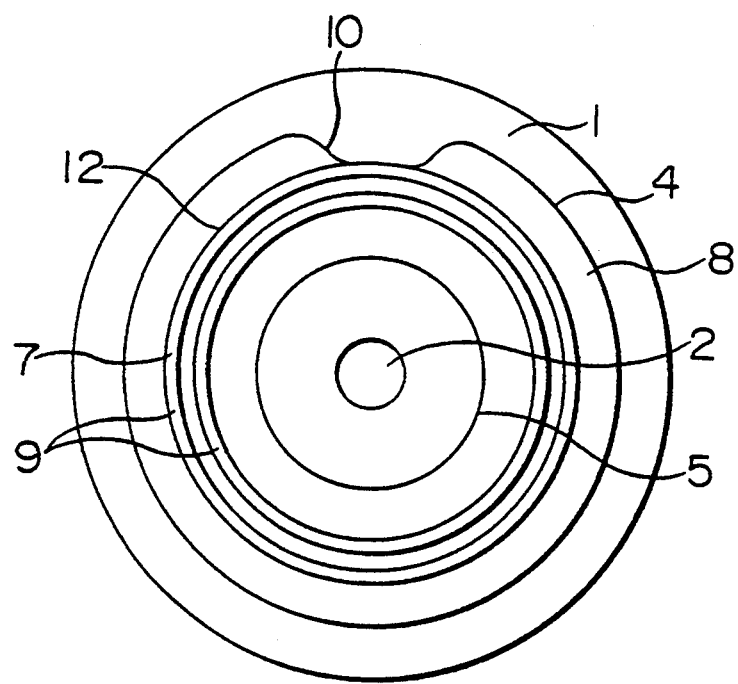
FIG. 3 is a front elevational view of the first member of the ostomy appliance of FIG. 1, showing an alternative flange construction therefor.

FIG. 3 shows an alternative embodiment of the first or adhesive plate member 1 in which the portions thereof corresponding to the portions of the embodiment shown in FIG. 1(a) and FIG. 2 are referenced by the same numerals. This embodiment differs from the embodiment shown in FIG. 1(a) and FIG. 2 in that in the embodiment shown in FIG. 3, the adhesive plate member 1 is round in shape, and includes only one cut-away recess or notch 10, which notch 10 is curved or generally U-shaped in construction and extends to the outermost periphery 12 of the fitting portion 7.

As for the construction of the adhesive plate member 1, this member can be composed of any one of numerous conventional constructions which have hitherto been used, such as for instance, a plate consisting of a skin protective agent which is composed of a hydrophillic polymer and a hydrophobic viscous polymer and having an adhesive or sticky foam sheet or film thereon, or a plate having viscous reinforcing tape on a outer periphery thereof, a plate obtained by coating adhesive on a foam sheet or film, or a plate having on the surface thereof, a film such as a polyethylene, ethylene-vinyl acetate copolymer, ethylene-ethyl acrylate copolymer, ethylene-ethyl acrylate copolymer polypropylene, polyvinyl chloride, polyester, polyamide or the like, or a film on the surface thereof obtained by laminating appropriately the above-identified films may likewise be used.

As for the material used in the construction of the first flange, an ethylene-ethyl acrylate copolymer, ethylene-vinyl acetate copolymer, ethylene-ethyl acrylate copolymer, ethylene-methyl methacrylate copolymer, polyethylene, vinyl chloride, ethylene-acrylic acid copolymer, ethylene-methacrylic acid copolymer, polyethylene chloride or the like may be used. The thickness of the coupled or adhered portion (of the first flange member) is, preferably, not more than about 1 mm. For adhering or fixing the first flange to the adhesive plate, a variety of conventionally known means may be utilized such as a method of welding using heat, a method of welding a film forming part of the adhesive plate to the first flange using a high frequency welder or supersonic welder and a method of adhering or sticking the film to the adhesive plate, using adhesives, and the like.

The same material used in the construction of the first flange 4 may also be used for construction of the second flange 13. The bag 16 may be fixed to the second flange by means of thermal welding, high frequency welding, supersonic welding, or by adhesion with adhesives or the like.

As the fitting portions of the first and second flanges, not only the combination of projections and grooves as shown may be used, but also various other fitting structures can be utilized. Moreover, the shape of the fitting portions is not necessarily round, as shown, but alternatively can be of elliptical or other shape, as desired. Furthermore, a cap member, stopper member or the like may be set or used in place of the pouch or bag 16.

OPERATION

Figure 4:
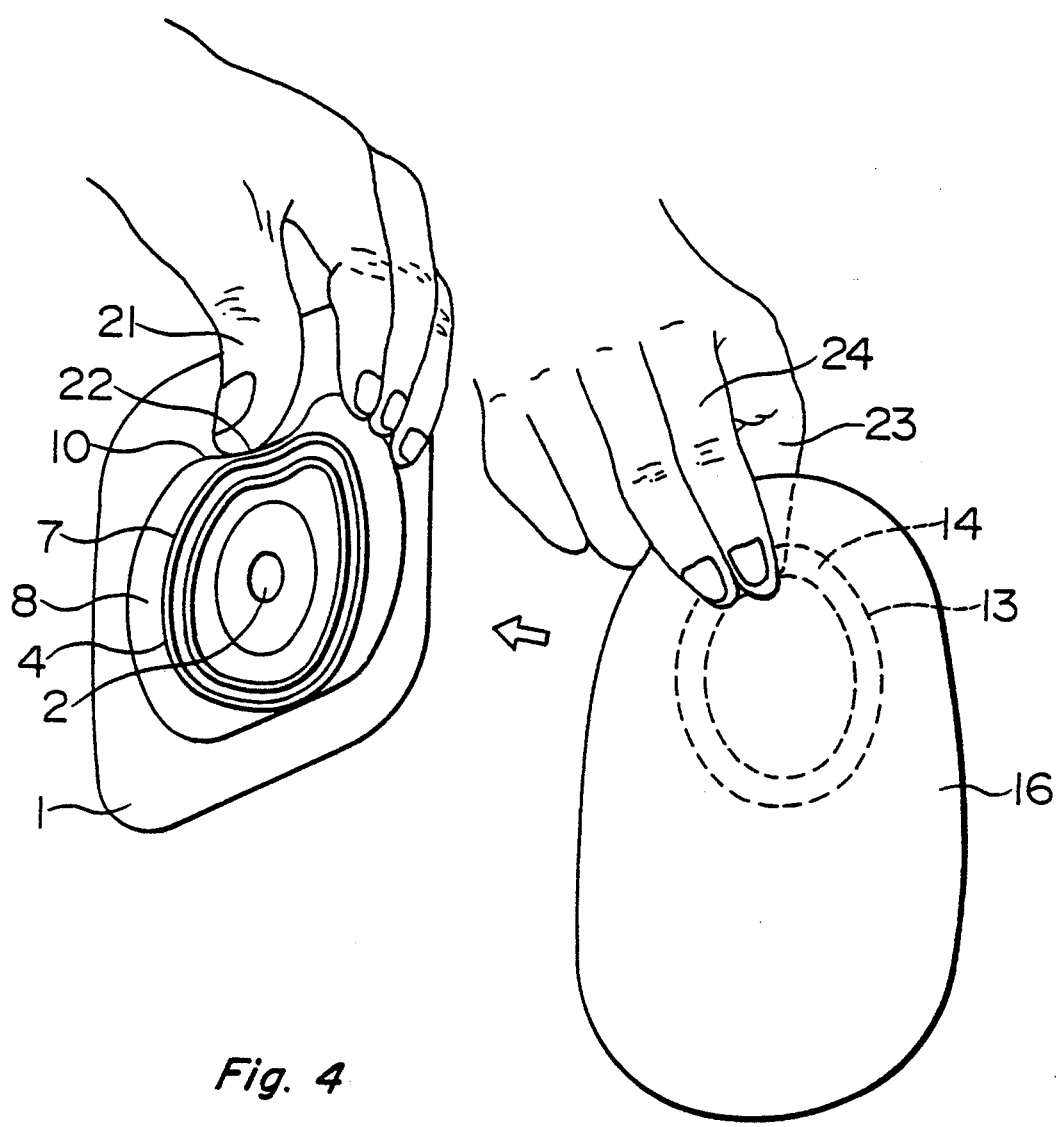
FIG. 4 is a perspective view of the ostomy appliance of FIG. 1, illustrating how the respective first and second members thereof can be held by a user to be joined together.

Operation and use of the present ostomy appliance will now be explained with reference to FIG. 4.

The adhesive plate 1 is adhered to a patient's skin so that the opening 2 thereof overlays or is superimposed on the desired aperture, for example, a stoma. The collar portion 8 of the first flange 4 can then be raised or lifted away from the non-adhesive side 6 of the adhesive plate, for instance using the thumb 21 of a first hand, wherein the belly of the thumb 21 touches a portion 22 of the notch 10 of the collar 8 which portion 22 is the closest possible to the fitting portion 7. The fitting portion 14 of the second flange 13 is pinched by and between fingers, such as for instance, the thumb 23 and the forefinger 24 of the other hand and then the thumb 23 is brought into contact with the thumb 21 on the first flange side, whereby the two fitting portions 7 and 14 are brought to the correctly aligned and opposed positions. The fingers of the first hand are then slid between the collar 8 and the adhesive plate 1, and the two fitting portions are pinched or pressed together successively therealong. In this way, the two fitting portions are fitted to each other without any pressing force acting on the patient's skin or the stoma.

The second flange is detached as follows: the collar portion 8 of the first flange 4 is supported by pinching it with the fingers or pressing it towards the adhesive plate side, while the second flange 13 is pulled by holding the tab 15 thereof with the fingers, whereby the second flange 13 can be easily detached without allowing any pulling force to act on the patient's skin or the stoma, or against the adhered portions of the adhesive plate and the first flange.

EFFECTS OF THE INVENTION

According to the present invention, the cut-away recess or notch provided in the collar portion associated with the first flange is utilized so as to ensure that the positional registration between the fitting portion of the first flange and the fitting portion of the second flange can be made easily yet accurately; the collar portion is utilized so as to ensure that the fitting or engagement between the two fitting portions can be effected without causing any pressing force to act on the human body; and, through the collar portion, it is made possible to ensure that the two fitting portions can be separated from each other without causing any pulling force to act on the human body and the mutually adhered portions of the adhesive plate and the first flange. Thus, the operation of mounting and demounting the ostomy appliance can be very easily carried out without giving pain to the patient.

What is claimed is:

1. Ostomy appliance comprising an adhesive plate fixably positionable by adhesion around the aperture of a human body, a first flange attached to the non-adhesive side of said adhesive plate, and a second flange capable of fitting to said first flange,
    said adhesive plate having an opening corresponding to the aperture of the human body,
    said first flange being fixed to said adhesive plate and extending outwardly nearly along the surface of said adhesive plate, said first flange having a ring-form fitting portion on the side opposite to said adhesive plate and extending around the opening of said adhesive plate, said ring-form fitting portion having an outermost periphery extending therearound and around said opening, a collar portion extending around at least one portion of the ring-form fitting portion, said collar portion have a cut-away recess in at least a portion thereof, said cut-away recess reaching the outermost periphery of said fitting portion and being of sufficient size as to allow a finger to be inserted therein, and
    said second flange having a ring-form fitting portion on one side thereof engageable with the fitting portion of said first flange, said cut-away recess being positioned so as to enable placement of a finger against the outermost periphery of the fitting portion of said first flange to enable aligning said fitting portions for engagement.

2. The ostomy appliance of claim 1 wherein the second flange has an ostomy bag attached thereto.

3. The ostomy appliance of claim 1 wherein the second flange has a cap attached thereto.

4. An ostomy appliance comprising first and second members, said first member including an adhesive plate having opposite first and second surfaces and an aperture extending therethrough, the first surface being adhesively fixable to a human body around an opening therein, the aperture extending through the adhesive plate corresponding approximately in size to the opening in the human body,
    a flange attached to said adhesive plate around the aperture extending therethrough, said flange extending outwardly from the aperture adjacent the second surface of said adhesive plate, said flange having first annular fitting means extending around the aperture opposite said adhesive plate, the first annular fitting means having a first outer peripheral edge extending therearound and around said aperture, the flange having a collar extending outwardly from one or more portions of the first outer peripheral edge, the collar forming at least one notch extending inwardly to adjacent the first outer peripheral edge, the notch being sufficiently large to enable a finger to be positioned therein adjacent to the first outer peripheral edge, and said second member having second annular fitting means cooperatively and sealably engageable with the first annular fitting means for detachably fitting the second member to the first member, the second annular fitting means having a second outer peripheral edge, said notch being positioned to enable a finger positioned therein to be used to align the first and second outer peripheral edges for cooperatively engaging the first and second annular fitting means, said notch being further positioned to enable movement of the finger without leaving the fitting means to a position between said adhesive plate and said flange to enable the finger to be used to facilitate engagement of the fitting means.

5. The ostomy appliance of claim 4 wherein said second member includes on ostomy bag.

6. The ostomy appliance of claim 4 wherein said second member includes a cap.

7. The ostomy appliance of claim 4 wherein the notch has a substantially linear shape.

8. The ostomy appliance of claim 4 wherein the collar forms a pair of opposing substantially linearly shaped notches.

9. The ostomy appliance of claim 4 wherein the second outer peripheral edge is dimensioned to correspond approximately to the size of the first outer peripheral edge.

10. The ostomy appliance of claim 4 wherein the flange is attached to the adhesive plate by an annular member.

11. An ostomy appliance comprising a first member including an adhesive plate having first and second opposed surfaces, the first surface being fixable by adhesion to a human body around an opening therein, and an aperture extending through said adhesive plate corresponding in size to an opening in an human body, a first flange attached to said adhesive plate around the aperture extending therethrough, said first flange extending radially outwardly relative to the aperture along said second surface, said first flange having first annular fitting means extending around the aperture opposite said adhesive plate and a first outer peripheral edge extending round the annular fitting means, a tab extending outwardly from a portion of the first outer peripheral edge, the tab having at least one truncated portion abutting the first outer peripheral edge, a second member having a second flange with second annular fitting means thereon and a second outer peripheral edge therearound, said second annular fitting means being cooperatively engageble with the first annular fitting means for detachably fitting the first and second members together, said truncated portion being of such a size to enable a finger to be positionable therein against the first and second members to guide the members into engagement with each other.

12. An ostomy appliance having a first member for attaching to the skin of a patient, said first member having an aperture therethrough and an annular flange portion extending around said aperture, said annular flange portion having an outer peripheral edge extending therearound and around said aperture, a portion extending outwardly from said annular flange adjacent one side thereof for attaching to the skin of the patient, and a bag member having an attachment portion including an annular flange portion for matingly engaging the annular flange portion on the first member when the respective annular flange portions are pressed together, the improvements comprising means for aligning by feel the annular flange portion of the bag member with the annular flange portion on the first member to facilitate engagement of the respective flange portions, said alignment means including a collar extending around at least a portion of the outer peripheral edge of said annular flange portion, said collar having a cut-out portion extending to the outer peripheral edge of the annular flange portion on the first member said cut-out portion being sufficiently large to enable insertion of a finger therein for aligning the respective edges of the annular flange portions on the first member and on the bag member.

* * * * *

UNITED STATES PATENT AND TRADEMARK OFFICE
CERTIFICATE OF CORRECTION

PATENT NO. : 5,356,399
DATED : October 18, 1994
INVENTOR(S) : Tetsuya Takahashi

It is certified that error appears in the above-identified patent and that said Letters Patent is hereby corrected as shown below:

Column 7, line 16, "on" should be --an--.

Column 7, line 36, "an" (2nd occurrence) should be --a--.

Signed and Sealed this

Third Day of January, 1995

Attest:

BRUCE LEHMAN

Attesting Officer

Commissioner of Patents and Trademarks